United States Patent [19]

Hill

[11] 4,078,560
[45] Mar. 14, 1978

[54] PEDIATRIC ARM RESTRAINT AND METHOD OF USING SAME

[75] Inventor: Edward J. Hill, 1515 David Whitney Bldg., Detroit, Mich. 48226

[73] Assignee: Arnold, White & Durkee, Houston, Tex.

[21] Appl. No.: 711,496

[22] Filed: Aug. 4, 1976

[51] Int. Cl.² ............................................. A61F 13/00
[52] U.S. Cl. .................................................. 128/133
[58] Field of Search ................................ 128/132–135

[56] References Cited

U.S. PATENT DOCUMENTS

| | | | |
|---|---|---|---|
| 2,998,008 | 8/1961 | Klesa | 128/133 |
| 3,008,466 | 11/1961 | Adam | 128/133 |
| 3,010,452 | 11/1961 | Smith | 128/133 |
| 3,297,026 | 1/1967 | Van Pelt | 128/133 |

*Primary Examiner*—Lawrence W. Trapp
*Attorney, Agent, or Firm*—Arnold, White & Durkee

[57] ABSTRACT

A pediatric arm restraint is disclosed for restricting movement of an infant's arm at the elbow. The restraint includes an inner foam pad and an outer stiff rigidifying plastic sheet, the foam pad being the larger of these two components to extend beyond the edges of the plastic sheet for comfort to the infant. A generally arcuate contour is provided on one edge of the restraint for placement in the infant's axilla, and the other end of the restraint extends beyond the elbow to essentially the wrist. The restraint is normally flat for ease in shipping and handling, but is easily bent into a tubular configuration around an infant's arm and then secured in that position by Velcro strips.

6 Claims, 2 Drawing Figures

PEDIATRIC ARM RESTRAINT AND METHOD OF USING SAME

BACKGROUND OF THE INVENTION

1. Field of the Invention

This invention relates generally to an arm restraint, and more particularly to a light weight, durable, comfortable, and disposable arm restraint for infants.

2. The Prior Art

Pediatricians and hospital personnel have long been confronted with the problem of restricting an infant's hands following surgery or during an intravenous feeding. Infants, by their natural curious nature, always try to pull at intravenous feedings tubes or medical dressings, thereby drastically reducing their effectiveness and requiring further medical attention.

Various prior attempts have been made to solve this problem, but no truly successful remedies have heretofore emerged.

One such attempt included merely placing a sock over the infant's hands and arms. This, however, is not truly effective and desirable because the sock is easily removed and because the infant is unable to use its hands for permissible activity while the sock is on the arm.

A second attempt included the use of splints and gause wrapping to keep the elbow straight, but this technique is both time consuming to the pediatrician and relatively uncomfortable to the young patient.

Another attempt involves the use of two semi-cylindrical medical metals frames which are placed around the infant's arm and taped in place to keep the elbow straight. Likewise, this particular effort has proved to be undesirable because (1) the end of the metal frames irritate the infant's axilla region, (2) the frames are heavy, particularly to the young patient, and (3) this device is relatively expensive.

In short, no suitable prior art device restricts the movement of an infant's elbow while also permitting free use of the infant's hands.

SUMMARY OF THE INVENTION

These prior art problems are eliminated by the present invention, which relates to a pediatric arm restraint including an inner foam pad affixed to an outer, overlying and rigidifying plastic sheet that can be wrapped into tubular form to cover the entire arm and then secured into position.

The inner foam pad, which is essentially rectangular and relatively thin, is placed against the infant's arm to provide a non-irritating cushion. The plastic sheet is likewise rectangular, but is flexible and deformable, yet relatively stiff in order to stiffen and rigidify the arm restraint, particularly when wrapped around the patient's arm in tubular form.

The foam pad and the plastic sheets are secured to one another in overlying, generally aligned manner, with the foam pad being dimensioned to extend beyond the outer edges of the plastic sheet to provide cushion protection from those edges. One edge of the arm restraint includes an arcuate indented contour to provide a curved edge for placement in the axilla of the infant. Securing means are also carried by the plastic sheet for releasably maintaining the arm restraint in the tubular, wrapped position to restrict the arm movement at the elbow over the desired period of time.

In the preferred embodiment, both the foam pad and the plastic sheet include respective, aligned, generally arcuate indentations along one of their corresponding, respective edges to provide the curved edge on the body portion.

Additionally, the securing means in the preferred embodiment is comprised of two pairs of cooperating, complementary Velcro strips secured to the outer surface of the plastic sheet by rivets. One strip in each of the pairs is secured by rivets at each of their ends at a position which is completely in the boundary formed by the edges of the plastic strip. The other strip in each of those pairs is secured to the plastic sheet adjacent one of its edges so that the strips extend beyond the edge to overlap and interlock with the other of the strips when the arm restraint is wrapped around the patient's arm. In this preferred arrangement, the rivets extend through the Velcro strips, the plastic sheet and the foam pad to provide a dual purpose—to secure the Velcro strips to the body portion of the arm restraint and to secure the foam pad to the plastic sheet.

An optional opening may be provided through the body portion of the restraint for receiving a cord which can be attached to a fixture, such as a bedpost, to restrain the movement of the infant's arm at the shoulder.

The method of using the invention includes bending the arm restraint from its initial, essentially flat shape into an essentially tubular shape to cover the infant's arm from the axilla to the wrist, with the curved edge of the body portion being placed within the axilla region. Then, the arm restraint is secured in the tubular position by suitable securement means to provide prolonged restraint of movement to the elbow. During use, the restraint prevents the infant patient from bending its elbows, and therefore prevents the infant from placing its hands in prohibited regions. Eventually, the arm restraint is removed from the infant's arm by releasing the securing means and then bending the arm restraint from the generally tubular configuration.

Accordingly, the present invention provides the following desirable advantages which have heretofore been missing in the prior art. First, the present pediatric arm restraint is light weight and comfortable as a result of the overall design and selection of materials. The arm restraint is also inexpensive and may therefore be disposed of after use with a particular patient. Equally as important, the present arm restraint is easy to use, both in placement around the patient's arm and in its removal. Yet another advantage is that this restraint is non-irritating to the infant patient and allows free use of the hands for permissible activity, such as holding toys.

These and other meritorious features and advantages will become more apparent from the following detailed description of the pediatric arm restraint, and the appended claims.

DETAILED DESCRIPTION OF THE PREFERRED EMBODIMENT

Figure 1:
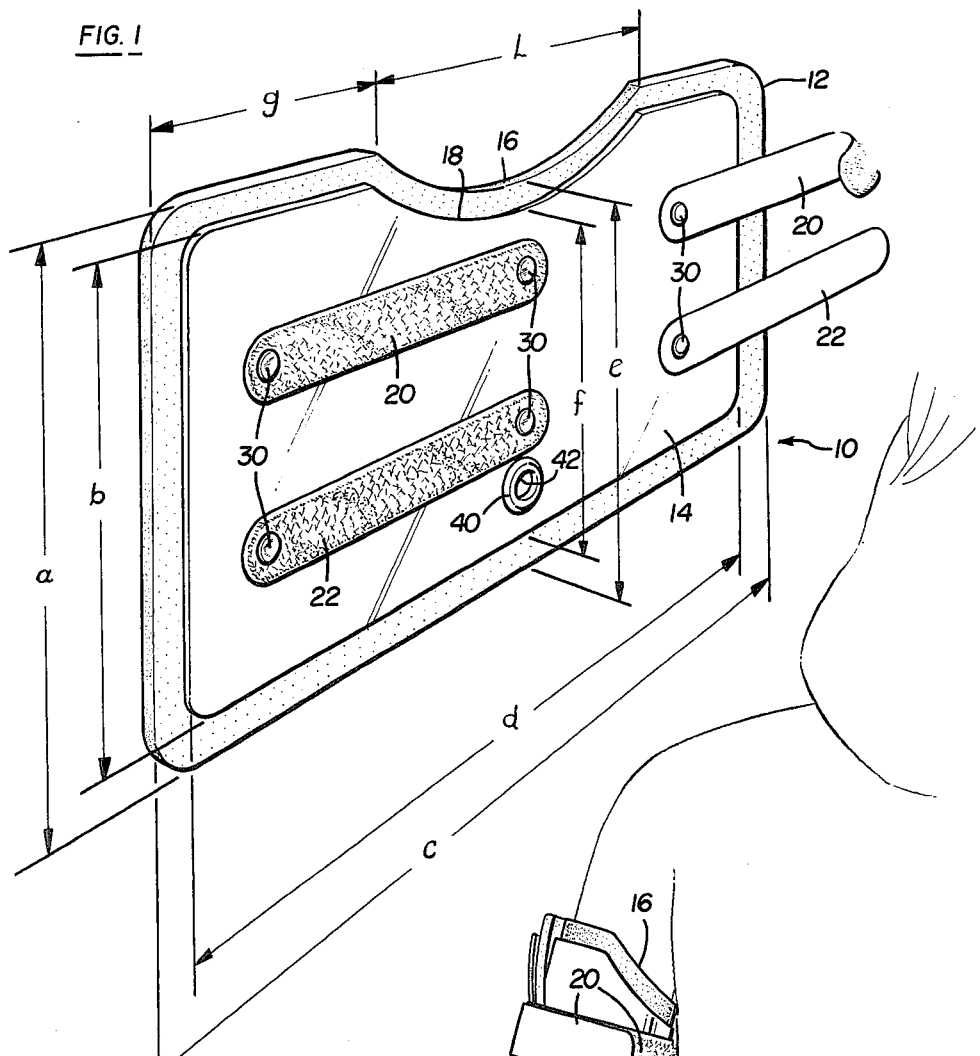
FIG. 1 is a perspective view of the pediatric arm restraint, in generally flat configuration prior to being placed around a patient's arm.

Referring now more particularly to the drawings, the pediatric arm restraint of this invention is shown by reference numeral 10 in a generally flat position in FIG.

Figure 2:
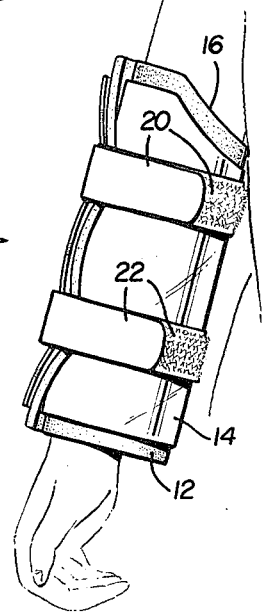
FIG. 2 illustrates the arm restraint in generally tubular configuration around a patient's arm.

1 prior to being placed in use on an infant's arm, as shown in FIG. 2.

The arm restraint 10 includes a generally rectangular cushion pad 12 which is interconnected to a generally rectangular rigidifying cuff 14. As illustrated, the cushion pad is at least slightly larger than the cuff in order to provide a cushioning border so that the edges of the rigidifying cuff will be spaced from the user's skin to prevent irritation. Any suitable soft cushion material may be used for the cushion pad 12, such as foam rubber. In the preferred embodiment, a sheet of polyethylene foam is proposed, such as that sold under the trade name Ethafoam by Dow Chemical Co. Likewise, the rigidifying cuff may be comprised of any suitable material which is flexible and deformable, yet stiff for providing the desired arm restraint. A specific example of such a material is polypropylene.

As can be seen from FIG. 1, the arm restraint 10 includes a contoured region 16 in the form of an arcuate depression, which is designed for fitting within the axilla (i.e. arm pit) of the infant. In the preferred embodiment, the rigidifying cuff likewise includes a similar, complementary shaped arcuate contour 18.

Two sets of cooperating attachment straps 20 and 22, which in the disclosed embodiment are straps sold under the trade name Velcro, are suitably secured to the arm restraint 10 to serve as securing means to maintain the arm restraint in the generally tubular restraining position when in use, as shown by FIG. 2. In the preferred embodiment, the Velcro straps are secured to the arm restraint by rivets 30, which extend through the straps, the rigidifying cuff 14 and the cushion pad 12. Thus, the rivets 30 serve two purposes; first, they secure the Velcro straps to the arm restraint and secondly, they secure the rigidifying cuff and the cushion pad to each other.

To use the arm restraint 10, a pediatrician or other medical personnel simply needs to wrap the arm restraint around the infant's arm and interlock the Velcro straps. Ideally, the arm restraint should be dimensioned so that it extends substantially from the shoulder region to the wrist to provide the necessary restraining support to the arm to prevent the infant from bending its elbow, thus preventing the infant from placing its hands in restricted regions. Accordingly, the contoured region 16 will be placed in the axilla and the other end of the arm restraint will extend below the elbow to substantially the wrist.

Naturally, different sized arm restraints 10 may be made to accommodate different aged and different sized infants. For example, the dimensions for a typical arm restraint which could be used for an infant under one year old is as follows, in reference to the dimensions shown in FIG. 1;

Dimension "a" is the height of the cushion pad and is approximately 5 inches;

Dimension "b" is the height of the rigidifying cuff and is approximately 4½ inches;

Dimension "c" is the wrap-around length of the foam cushion pad and is approximately 7½ inches;

Dimension "d" is the wrap-around length of the rigidifying cuff and is approximately 7¼ inches;

Dimension "e" is the height of the arm restraint at the position of the contoured recess and is approximately 4¼ inches;

Similarly, Dimension "f" is the height of the plastic cuff at the contoured recess and is approximately 3¾ inches.

Dimension "g" is about two inches and dimension "h" is about 3½ inches.

Thus, it can be seen that the difference between dimensions "a" and "b" and "c" and "d" and "e" and "f" are approximately ½ inch, providing a border all the way around the rigidifying cuff 14 of approximately ¼ inch. Of course, these dimensions will be enlarged for older infants. For example, dimension "a" in a restraint for an over one-year old infant would be approximately 7 inches, with the other dimensions being varied substantially proportionally.

An optional feature is shown by reference numeral 40, which includes an enlarged rivet providing an opening 42. In the event that it is desirable to completely restrain movement of the infant's arm, a cord can be inserted through opening 42 and appropriately tied to a fixture, such as a bed post. In this situation, the arm restraint prevents movement of the elbow, and the cord will prevent movement of the arm at the shoulder.

Thus, it is apparent that the present arm restraint provides numerous advantages, which have been elaborated on in earlier portions of this disclosure. Additionally, it is to be understood that this disclosure is exemplary in nature and limited only by the following appended claims.

Having therefore completely and sufficiently disclosed my invention, I now claim:

1. A pediatric arm restraint for wrapping around an infant's arm to maintain the elbow straight so that the infant is unable to place its hand on restricted regions, such as intravenous feedings or medical dressings, comprising:

an essentially rectangular body portion which is normally flat for shipping and deformable for wrapping completely around an infant's arm to form an essentially tubular elbow restraint, with the body portion being adapted to extend from the infant's axilla to below the elbow essentially to the wrist yet permitting freedom of movement of the arm at the shoulder and freedom of movement at the fingers and wrist, the body portion including (a) an inner pad of essentially rectangular, relatively thin foam material for placement against the infant's arm to provide a non-irritating cushion and (b) an essentially rectangular sheet of flexible, deformable, yet relatively stiff plastic material for rigidifying the arm restraint;

the foam pad and the plastic sheet being interconnected in overlying generally aligned manner, with the foam pad being only slightly larger than the plastic sheet and extending laterally beyond essentially the entire periphery of the plastic sheet to provide a cushion protection from the sheet edges;

the foam pad having a pair of major edges and a pair of minor edges, a generally arcuate indentation being along one of the major edges to provide a curved edge on the body portion for placement against the axilla of the infant;

the plastic sheet being integral, being sized to extend generally from the infant's axilla region to below the elbow, and being continuous in the region of the elbow to restrict elbow movement; and securing means carried by the plastic sheet for releasably maintaining the arm restraint in the tubular, wrapped position around the infant's arm.

2. The arm restraint defined in claim 1, wherein the plastic sheet has a pair of major and minor edges, a generally arcuate indentation being along one of the major edges adjacent the indentation on the foam pad.

3. The arm restraint as defined in claim 2, further including an opening through the plastic sheet and foam pad to receive a cord for securing the arm restraint, while wrapped around a patient's arm, to a fixture to accommodate the restraint of movement of the infant's arm at the shoulder.

4. The arm restraint defined in claim 1, characterized by said securing means being comprised of two pairs of cooperating, complementary Velcro strips, one strip of each of said pairs being secured to the outer surface of the plastic sheets by rivets and being positioned completely within the boundary formed by the edges of the plastic sheet, the other strip of each of said pairs being secured to the outer surface of the plastic sheet by a respective single rivet adjacent one edge of the plastic sheet so that the said other strips extend beyond one edge of the arm restraint to permit their overlapping and interlocking with the said one strip in said pairs when the arm restraint is wrapped around the patient's arm, and said rivets extending through the Velcro strips, the plastic sheet and the foam pad (a) to secure the Velcro strips to the body portion of the arm restraint and (b) to secure the foam pad to the plastic sheet.

5. The arm restraint as defined in claim 4, characterized by said foam pad being comprised of polyethylene foam and said plastic sheet being comprised of polypropylene.

6. In a method of restraining the movement of an infant's elbow, by the steps of:

bending a pediatric arm restraint from an essentially flat shape into an essentially tubular shape to cover the infant's arm essentially from the shoulder to the wrist, the pediatric arm restraint including an inner pad of essentially rectangular relatively thin foam material placed against the infant's arm to provide a non-irritating cushion and an essentially rectangular sheet of flexible, deformable yet relatively stiff plastic material for rigidifying the arm restraint, the foam pad and the plastic sheet being interconnected and overlying in generally aligned manner with the foam pad being at least slightly larger than the plastic sheet and extending laterally beyond essentially the entire periphery of the plastic sheet to provide a cushion protection from the edges of the plastic sheet, the foam pad having a generally arcuate contour along one of its edges to provide a curved edge for placement in the infant's axilla, and the plastic material being integral and including an elbow portion which is relatively rigid along the axis of the arm when the arm restraint is bent to cover the infant's arm, the elbow portion of the plastic sheet being continuous to restrict elbow movement;

positioning the curved edge of the arm restraint in the axilla of the infant and positioning the elbow portion of the plastic sheet in alignment with the infant's elbow to restrain essentially all elbow movement;

securing the arm restraint in the tubular position around the infant's arm with securement means to provide prolonged restraint of movement to the infant's elbow; and then later removing the arm restraint from the infant's arm by (a) releasing the securement means and (b) bending the arm restraint from the generally tubular configuration.

* * * * *

UNITED STATES PATENT OFFICE
CERTIFICATE OF CORRECTION

Patent No. 4,078,560　　　　　　　　　Dated　March 14, 1978

Inventor(s)　Edward J. Hill

It is certified that error appears in the above-identified patent and that said Letters Patent are hereby corrected as shown below:

The firm name of Arnold, White & Durkee be removed as Assignee.

Signed and Sealed this

Twenty-ninth Day of August 1978

[SEAL]

Attest:

RUTH C. MASON
Attesting Officer

DONALD W. BANNER
Commissioner of Patents and Trademarks